(12) United States Patent  (10) Patent No.: US 9,055,907 B2
Piech  (45) Date of Patent: Jun. 16, 2015

(54) SURGICAL ACCESS PORT

(71) Applicant: Cook Medical Technologies LLC, Bloomington, IN (US)

(72) Inventor: David Piech, Durham, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 175 days.

(21) Appl. No.: 13/683,460

(22) Filed: Nov. 21, 2012

(65) Prior Publication Data

US 2013/0137932 A1 May 30, 2013

Related U.S. Application Data

(60) Provisional application No. 61/564,021, filed on Nov. 28, 2011.

(51) Int. Cl.
*A61B 17/34* (2006.01)
*A61B 1/32* (2006.01)

(52) U.S. Cl.
CPC ............ *A61B 1/32* (2013.01); *A61B 17/3423* (2013.01); *A61B 2017/3435* (2013.01); *A61B 2017/3466* (2013.01); *A61B 2017/3486* (2013.01)

(58) Field of Classification Search
USPC .......................................... 600/204, 207, 208
See application file for complete search history.

(56) References Cited

U.S. PATENT DOCUMENTS

| | | | |
|---|---|---|---|
| 4,324,262 A | | 4/1982 | Hall |
| 5,853,395 A | * | 12/1998 | Crook et al. ................. 604/174 |
| 6,440,063 B1 | | 8/2002 | Beane et al. |
| 7,300,399 B2 | | 11/2007 | Bonadio et al. |
| 2005/0137609 A1 | | 6/2005 | Guiraudon |
| 2005/0192483 A1 | | 9/2005 | Bonadio et al. |
| 2009/0221966 A1 | | 9/2009 | Richard |
| 2010/0312066 A1 | * | 12/2010 | Cropper et al. ............... 600/207 |

OTHER PUBLICATIONS

PCT International Search Report and Written Opinion for International No. PCT/US2012/065987, date of mailing Apr. 9, 2013, 18 pgs.
Advanced Surgical Concepts, Triport Brochure, Rev. 00, 1 pg.
Single Port Cholecystectomy videos, www.womsurgical.com, 1 pg., website last visited Nov. 20, 2012.
Covidien SILS port, www.covidien.com/silsport/pages.aspx, 1 pg., website last visited Nov. 21, 2012.
International Preliminary Report on Patentability for PCT/US2012/065987 issued Jun. 3, 2014, 11 pgs.

* cited by examiner

*Primary Examiner* — Andrew Yang
(74) *Attorney, Agent, or Firm* — Brinks Gilson & Lione

(57) ABSTRACT

The present embodiments provide a surgical access port comprising at least one channel having proximal and distal ends, and a lumen extending therebetween. The at least one channel comprises a first state in which the proximal end is positioned proximal to the distal end, and comprises a second state in which the at least one channel is everted by advancing the proximal end through the distal end, such that the proximal end is positioned distally beyond the distal end. An expansion member of the surgical access port is configured for insertion through a surgical incision in a contracted state, and expands to a diameter larger than the surgical incision in an expanded state. In one embodiment, the expansion member comprises a toroidal balloon that comprises a material adapted to flex and conform to tissue distal to the surgical incision in the expanded state.

19 Claims, 3 Drawing Sheets

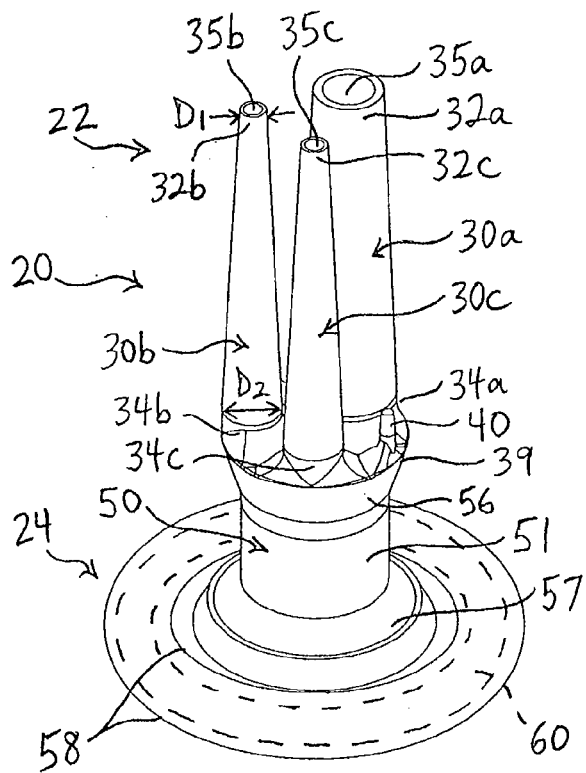
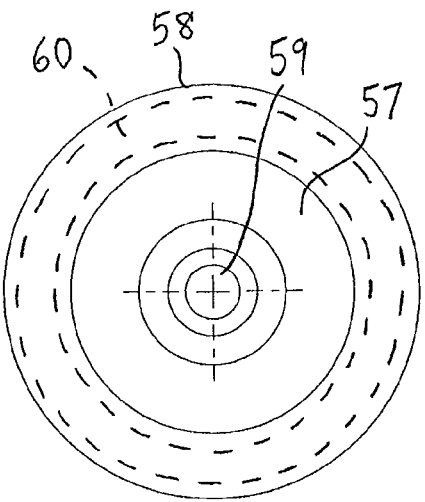
FIG. 1   FIG. 2
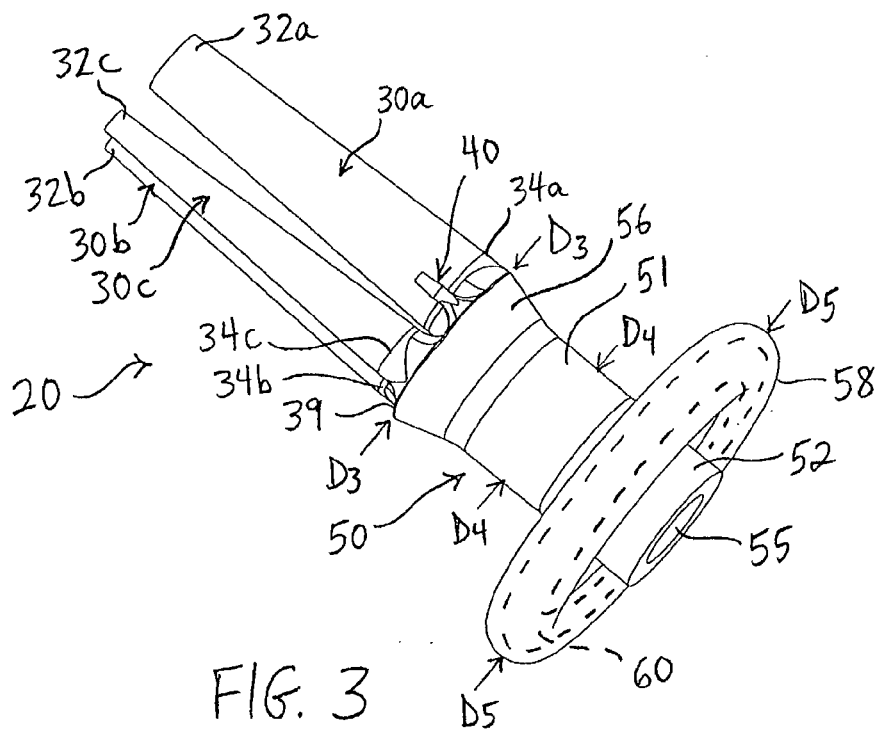
FIG. 3

SURGICAL ACCESS PORT

PRIORITY CLAIM

This invention claims the benefit of priority of U.S. Provisional Application Ser. No. 61/564,021, entitled "Surgical Access Port," filed Nov. 28, 2011, the disclosure of which is hereby incorporated by reference in its entirety.

BACKGROUND

The present embodiments relate generally to medical devices, and more particularly, to a surgical access port for inserting one or more instruments through an opening into a patient's bodily cavity.

Surgical incisions may be made in tissue to access an array of bodily cavities using various techniques. For example, it may desirable or necessary to access a patient's bodily cavity within the peritoneum using one or more incisions made in the abdomen.

In a conventional open procedure, a relatively large incision is made in the abdominal wall. A surgeon may visualize the target site directly, and may insert his or her hands, along with one or more instruments, directly into the abdominal cavity using this technique. The relatively large incision formed from the open procedure may result in increased trauma and healing time, as well as increased scarring of the patient.

As an alternative to an open procedure, an array of minimally invasive techniques have been used to access a patient's bodily cavity, such as the abdominal cavity. For example, in a laparoscopic procedure, the insertion of a laparoscope allows doctors to perform surgeries using a few relatively small incisions into the abdomen. One of the incisions may be for insufflation of the abdominal cavity with gas to elevate the abdominal wall relative to the internal organs to create additional room for viewing and manipulating instruments. Other incisions may be for viewing devices and/or other instruments for treating organs or tissue within the bodily cavity. A few of the advantages of laparoscopic surgery, relative to an open procedure, are reduced trauma and healing time, as well as reduced scarring of the patient.

Recently, newer surgical methods have been developed allow a single "port" to permit insertion of viewing devices and treatment instruments into the bodily cavity. In contrast to laparoscopic techniques that involve the formation of multiple incisions, this newer technique involves the creation of a single incision, and the port then manages the use or insertion of various components, e.g., for insufflation, visualization and treatment of tissue and/or organs. Such a single incision port technique is promising for the further reduction in trauma and scarring, but as a relatively new technique, there are areas of improvements to enhance simplicity and ease of use.

SUMMARY

The present embodiments provide a surgical access port comprising at least one channel having proximal and distal ends, and a lumen extending therebetween. In one embodiment, the at least one channel comprises a first state in which the proximal end is positioned proximal to the distal end, and comprises a second state in which the at least one channel is everted by advancing the proximal end through the distal end, such that the proximal end is positioned distally beyond the distal end. In one exemplary embodiment, the proximal end of the at least one channel has a first outer diameter and the distal end of the at least one channel has a second inner diameter, where the first outer diameter is smaller than the second inner diameter. In one embodiment, first, second and third channels are provided, and one or more of the channels may be capable of eversion.

The surgical access port also comprises at least one expansion member configured for insertion through a surgical incision in a contracted state, and that expands to a diameter larger than the surgical incision in an expanded state. In one embodiment, the at least one expansion member comprises a toroidal balloon that comprises a material adapted to flex and conform to tissue distal to the surgical incision in the expanded state.

The surgical access port may comprise a proximal region, where the at least one channel is positioned in the first state, and may comprise a distal region, where the at least one expansion member is positioned. In one embodiment, a main conduit having a lumen extends from a junction near the proximal region distally through the expansion member. The lumen of the at least one channel is in fluid communication with the lumen of the main conduit. Further, in the second state, the proximal end of the at least one channel is everted distally through the lumen of the main conduit and distally through the expansion member.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 1 is an elevated perspective view of a first embodiment of a surgical access port, with an expansion member shown in an expanded state.

FIG. 2 is a view from the bottom towards the top of the surgical access port of FIG. 1.

FIG. 3 is a perspective view of the surgical access port of FIG. 1 from another angle.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patent's anatomy during a medical procedure.

Figure 4:
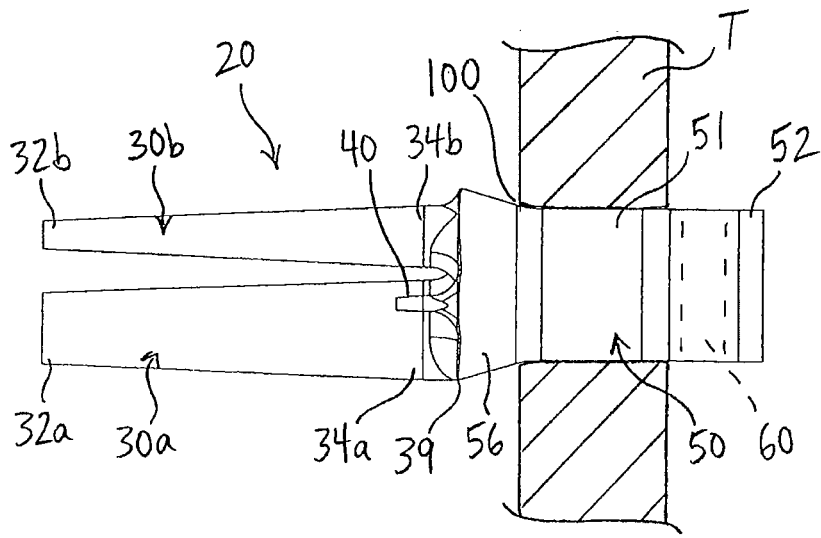
FIGS. 4-6 depict exemplary method steps for using the surgical access port of FIGS. 1-3, where the surgical access port is shown from a side view and a patient's tissue is shown from a side-sectional view.
Figure 5:
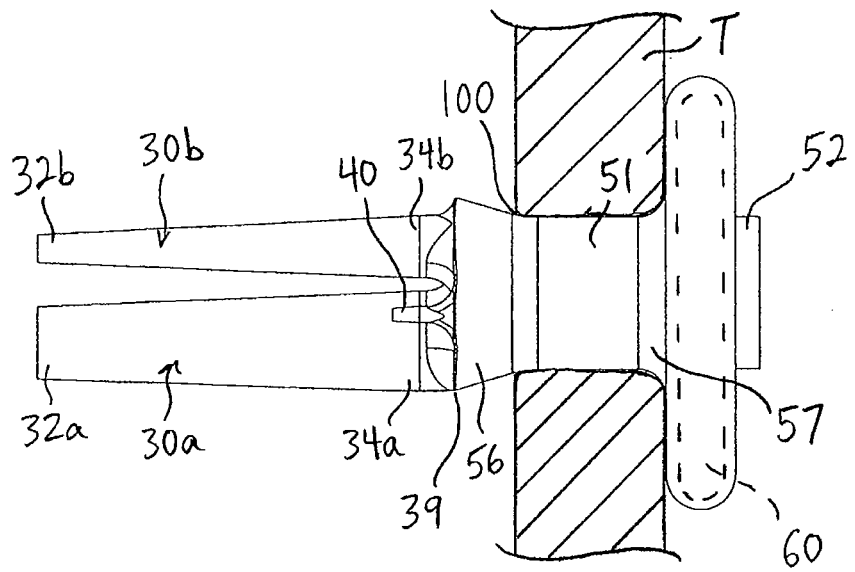
Figure 6:
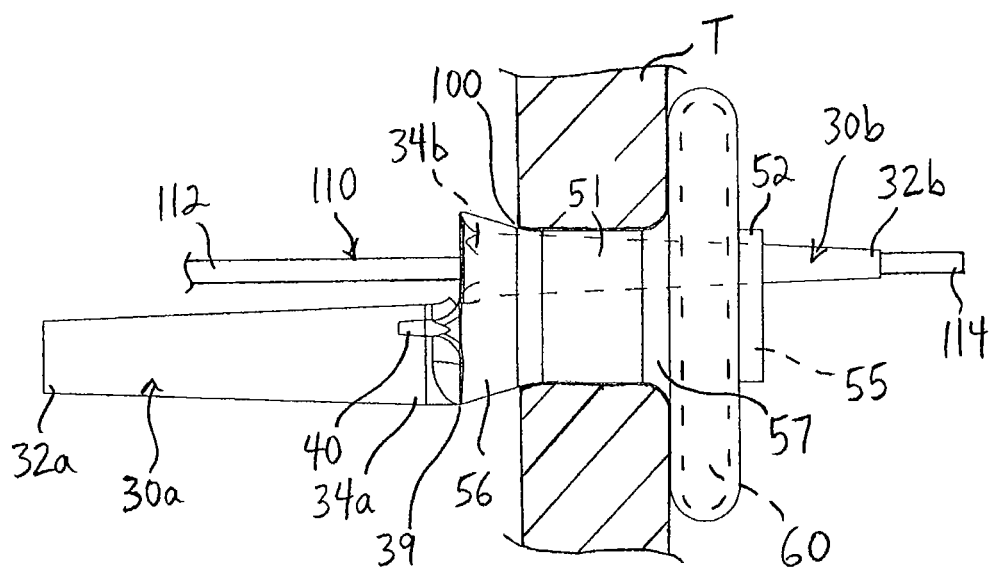

Referring to FIGS. 1-3, a first embodiment of a surgical access port 20 is shown. The surgical access port 20 comprises proximal and distal regions 22 and 24, respectively. When a plug region 51 of the surgical access port 20 is aligned with an incision formed in the patient, one or more components at the proximal region 22 are initially disposed external to the patient, while components at the distal region 24 are disposed internal to the patient, as shown in FIGS. 4-6 below.

The proximal region 22 of the surgical access port 20 comprises at least one channel that is configured for the insertion of one or more instruments. In the examples shown herein, the surgical access port 20 comprises a first channel 30a, a second channel 30b, and a third channel 30c. While three channels 30a-30c are depicted, it will be appreciated that greater or fewer channels may be provided, and their shapes and placements may be varied, without departing from the spirit of the present embodiments.

The first channel 30a comprises proximal and distal ends 32a and 34a, respectively, and a lumen 35a extending therebetween, as best seen in FIG. 1. Similarly, the second channel 30b comprises proximal and distal ends 32b and 34b, respectively, and a lumen 35b extending therebetween. The third channel 30c comprises proximal and distal ends 32c and 34c, respectively, and a lumen 35c extending therebetween. The distal ends 34a-34c of the channels 30a-30c, respectively, each terminate near a junction 39 of the surgical access port 20, as shown in FIGS. 1 and 3. As will be explained in further detail below, the lumens 35a-35c of the channels 30a-30, respectively, are each configured to permit the passage of one or more instruments through a surgical incision.

One or more of the channels 30a-30c may comprise a tapered shape between its proximal and distal ends. In the example of FIGS. 1 and 3, each of the channels 30a-30c comprises a generally uniform taper formed between its proximal and distal ends, from a smaller proximal diameter to a larger distal diameter. The configuration of the tapers may facilitate eversion of one or more of the channels 30a-30c. For example, in one embodiment, the proximal end 32b of the second channel 30b comprises a first outer diameter $D_1$, while the distal end 34b of the second channel 30b comprises a second inner diameter $D_2$, where diameter $D_2$ is greater than diameter $D_1$ as shown in FIG. 1, thereby subsequently facilitating eversion of the narrower proximal end 32b through the wider distal end 34b, as depicted in FIG. 6. In alternative embodiments, however, the first outer diameter $D_1$ at the proximal end 32b may be substantially equal to, or slightly greater than, the second inner diameter $D_2$ at the distal end 34b, and the proximal end 32b still may be everted through the distal end 34b, particularly if the material forming the channel 30b is flexible. In short, any combination of the channels 30a-30c may comprise a generally uniform diameter or a tapered shape, and any combination of the channels 30a-30c further may be evertable or non-evertable.

The surgical access port further comprises a main conduit 50 having a lumen 55. In one embodiment, the main conduit 50 extends from the junction 39 distally through an expansion member 60, as best seen in FIG. 3. In the embodiment shown, the main conduit 50 comprises a plug region 51 and an optional distal segment 52. The plug region 51 is configured to align with a surgical incision 100, as depicted in FIGS. 5-6, while the distal segment 52 extends through the expansion member 60 and distal to the surgical incision 100.

In an alternative embodiment, the distal segment 52 may be omitted, such that the plug region 51 of the main conduit 50 transitions directly into a second taper 57 disposed between the plug region 51 of the main conduit 50 and the expansion member 60. If the distal segment 52 is omitted, a physician may be able to insert instruments at a wider array of angles once inside a patient's bodily opening, i.e., without being limited in direction by the distal segment 52.

The lumens 35a-35c of the first, second and third channels 30a-30c, respectively, are each in fluid communication with the lumen 55 of the main conduit 50. Further, in the second state, at least one of the proximal ends 32a-34a of the first, second and third channels may be everted distally through the lumen 55 of the main conduit 50 and distally through the at least one expansion member 60, as shown in FIG. 6.

The at least one expansion member 60, disposed at the distal region 24 of the surgical access port 20, has expanded and contracted states. In the embodiments shown herein, an exemplary expansion member comprises a toroidal balloon 60. The toroidal balloon 60 has a contracted state, shown in FIG. 4, in which the balloon 60 is deflated for insertion through the surgical incision 100 in a patient. The toroidal balloon 60 further comprises an expanded state in which fluid is provided within interior confines of the toroidal balloon 60 to inflate the balloon into the ring-shaped configuration shown in FIGS. 1-3 and FIGS. 5-6.

In the embodiment utilizing a toroidal balloon 60, the surgical access port 20 further comprises an inflation port 40, which is coupled to an inflation source comprising a liquid or gas. In the embodiments shown, the distal ends 34a-34c of the channels 30a-30c, and the inflation port 40, terminate near the junction 39 of the surgical access port 20. This allows the inflation source to be coupled to the inflation port 40 at any time when the plug region 51 is disposed within the surgical incision 100, as shown in FIGS. 4-6. At least one tube or other conduit (not shown) may be provided to enable fluid communication between the inflation port 40 and the toroidal balloon 60.

In the expanded state, the toroidal balloon 60 comprises an outer diameter $D_5$, illustrated in FIG. 3, which is greater than a diameter of the surgical incision 100 formed in the patient, as depicted in FIGS. 5-6. As explained further below, the toroidal balloon 60 may comprise a material adapted to flex and conform to tissue distal to the surgical incision 100, thereby advantageously providing an effective seal, particularly during insufflation of the peritoneum of a patient.

While the at least one expansion member of the surgical access port 20 has been shown as an exemplary toroidal balloon 60, it will be appreciated that multiple different expansion members may be provided and may comprise features other than a balloon, such as ring or hook-shaped elements that may or may not be expandable. One example of an expansion member 60 having a ring-shaped element that may be expandable is a ring comprising a shape-memory material, such as a nickel-titanium alloy, that comprises a contracted state for advancement through a surgical incision, and self-expands to an expanded predetermined state when no longer radially constrained. In the expanded state, a diameter of the self-expanding ring is larger than the incision 100 to help secure a distal portion of the surgical access port 20 distal to the incision 100.

One example of an expansion member 60 having a ring-shaped element that may not be expandable is a ring comprising an elliptical shape, where one portion of the ellipse has a relatively small width and another portion of the ellipse has a relatively large width. In this embodiment, the portion of the ellipse having a relatively large width is inserted parallel to the surgical incision to fit therethrough. After advancement through the incision, the ring is rotated about 90 degrees so that the portion of the ellipse having a relatively large width is positioned perpendicular to the surgical incision to prevent retraction therethrough.

Further alternative expansion members 60 may comprise one or more expandable hooks or other elements capable of bowing radially outward distal to the opening 110 in an expanded state. It will be appreciated that still further alternative expansion members 60 may be provided without departing from the spirit of the present embodiments.

The surgical access port 20 may further comprise at least one membrane 58. In one exemplary embodiment, the membrane 58 comprises a relatively thin sheet of material that at least partially surrounds the expansion member 60. Optionally, the at least one membrane 58 may fully encase the expansion member 60. In one embodiment, the at least one membrane 58 may extend from the plug region 51 of the main conduit 50 distally over the expansion member 60, and then curl in a proximal and radially inward direction to at least partially or fully encircle the expansion member 60.

In one embodiment, the membrane 58 covers the expansion member 60 and extends proximally through the plug region 51 of the main conduit 50 and forms at least one of the components of proximal region 22. In particular, the membrane 58 may form one, two, or all three of the channels 30a-30c. In order to manufacture the surgical access port 20 in this manner, elastomer molding techniques may be used. One particular technique that may be used is injection molding, although other techniques may be employed.

In alternative embodiments, multiple different membranes and materials may be employed at different regions of the surgical access port 20. For example, one or more of the channels 30a-30c may comprise a relatively thin and/or flexible membrane that allows eversion of one or more of the channels 30a-30c, as described and shown with respect to FIG. 6. By contrast, the main conduit 50 may comprise a material ranging from relatively flexible to relatively rigid, yet which maintains a circumferential seal within the surgical incision 100 and maintains its position when one or more of the channels 30a-30c are everted through the main conduit 50. Further, the material of membrane 58 covering the expansion member 60 may be more flexible than the material of the main conduit 50, thereby enabling expansion of the toroidal balloon 60 or other expansion member within the membrane 58 without risk of deformation or rupture of the balloon or other member.

The membrane 58 may comprise a flexible material that provides an airtight seal and can withstand the pressure of insufflation. Properties for such a material, or composite of multiple materials, may include materials that expand with a low initial modulus of elasticity to approximately 120%-150% elongation, and then transition to a state with a higher modulus of elasticity, thus resisting further elongation. The initial elongation allows flexibility of the port so that instruments can be advanced through the port, and allows the insufflation pressure to push the plug region 51 against the tissue in the incision to create an airtight seal. By way of example and without limitation, the membrane 58 may comprise silicone rubber, or any similar elastomer including, for example, fluorosilicone rubber, nitrile, and the like, without limitation. Further, a composite of a fabric within silicone rubber may be used, in which case the rubber may provide initial elongation and an air-tight seal, and the fabric may provide a high ultimate tensile strength to prevent breakage.

The junction 39, where the distal ends 34a-34c of the channels 30a-30c and the inflation port 40 terminate, comprises an outer diameter $D_3$, illustrated in FIG. 3, which is slightly larger than an outer diameter of the surgical incision 100, as depicted in FIGS. 4-6. The plug region 51 of the main conduit 50 comprises an outer diameter $D_4$, illustrated in FIG. 3, which preferably is about the same diameter as the surgical incision 100, or slightly greater or smaller relative to the surgical incision, while allowing the plug region 51 of the main conduit 50 to reside at least partially within the surgical incision. A first taper 56 is disposed between the plug region 51 and the junction 39, as shown in FIG. 1. The first taper 56 prevents the junction 39 from being inserted into the surgical incision 100, as depicted in FIGS. 4-6. If the region 56 is made of a sufficiently elastic material, the region 56 may bulge outward under the insufflation pressure, increasing the diameter of the port immediately proximal to the incision at the skin, thus further preventing the port from slipping deep into the incision.

Further, a second taper 57 may be disposed between the plug region 51 of the main conduit 50 and the expansion member 60, as best seen in FIG. 1. The second taper 57 may provide a transition from the outer diameter $D_4$ of the plug region 51 of the main conduit 50 to the larger outer diameter $D_5$ of the at least one expansion member 60 in its expanded state.

Referring now to FIGS. 4-6, exemplary method steps are described in further detail for using the surgical access port 20 of FIGS. 1-3. In FIG. 4, a surgical incision 100 has been made in a patient's tissue T, which may comprise, by way of example and without limitation, abdominal tissue. The surgical incision 100 may be formed using techniques that are known in the art.

In a next step, the surgical access port 20 is provided with the expansion member 60 in the contracted state, and is advanced distally such that the expansion member 60 extends distally beyond the surgical incision 100, as shown in FIG. 4. At this time, at least a portion of the plug region 51 of the main conduit 50 is aligned within the surgical incision 100. Moreover, the first taper 56, which is disposed between the junction 39 and the plug region 51, may abut a proximal or outer surface of the patient's tissue T, as depicted in FIG. 4.

As noted above, an outer diameter $D_4$ of the plug region 51 preferably is about the same diameter as the surgical incision 100, or slightly greater or smaller relative to the surgical incision 100. An array of surgical access ports 20 may be provided in an operating setting and the outer diameter $D_4$ of the plug region 51 may be selected based on the size of the incision 100 being made in the tissue T.

Optionally, the surgical access port 20 may comprise at least one insufflation port that is capable of furnishing gas to the abdominal cavity during the procedure. The insufflation of the abdominal cavity with gas may be provided at this time to elevate the abdominal wall relative to the internal organs to create additional room for viewing and manipulating instruments.

Referring to FIG. 5, in a next step, the expansion member 60 of the surgical access port 20 is expanded. In the embodiments shown herein, in which the expansion member 60 comprises a toroidal balloon, an inflation source supplies liquid or gas to the toroidal balloon 60 via the inflation port 40, and any tubes or other conduits disposed between the inflation port 40 and the toroidal balloon 60. In the expanded state, the toroidal balloon 60 comprises the outer diameter $D_5$ that is greater than a diameter of the surgical incision 100.

Advantageously, the toroidal balloon 60 provides an effective distal seal for the surgical access port 20, particularly during insufflation of the peritoneum of a patient. In particular, the toroidal balloon 60 can be inflated a sufficient amount so that the associated membrane 58 presses against tissue T within the peritoneum, thereby maintaining a tight seal during insufflation. The toroidal balloon 60 comprises a material adapted to flex and conform to tissue distal to the surgical incision 100, even with tissue irregularities. The provision of the toroidal balloon 60 further advantageously eliminates the need to insert an oversized solid distal end of an access port through a smaller diameter incision in the hopes that the oversized distal end will achieve a seal once inside the bodily cavity.

Referring now to FIG. 6, in a next step, a first instrument 110 having proximal and distal ends 112 and 114 may be inserted into one of the lumens 35a-35c of the channels 30a-

30c. The first instrument 110 may comprise a camera or any other instrument to perform desirable operative functions inside of the patient's bodily cavity distal to the tissue T. In FIG. 6, the first instrument 110 is shown inserted through the lumen 35b of the second channel 30b.

The configuration of the taper of the channel 30b, along with its relative flexibility, allows the eversion of the relatively small diameter proximal end 32b distally through the relatively large diameter distal end 34b, as shown in FIG. 6. In effect, the channel 30b transitions from a first state in which the proximal end 32b is positioned proximal to the distal end 34b, to a second state in which where the proximal end 32b is inserted through and extends distally beyond the distal end 34b of the channel 30b.

In one embodiment, the membrane of each of the channels 30a-30c may be sized to appropriately couple with an associated instrument to create an airtight seal. In this instance, eversion may be achieved by first holding both the particular channel and the associated instrument during initial insertion of the instrument, and then letting go of the channel and advancing the instrument distally to achieve eversion.

Advantageously, in the second state of the channel 30b, the everted lumen 35b now tapers from a larger diameter at the original distal end 34b to a smaller diameter at the original proximal end 32b, and such a decreasing taper may facilitate further advancement of instruments. Additionally, the original proximal end 32b may extend distal to the expansion member 60 within the body cavity, as shown in FIG. 6. Since the channel 30b is flexible, the instrument 110 may be guided in any desired radial direction within the bodily cavity, with accompanying radial deflection of the proximal end 32b of the channel 30b within the bodily cavity.

Further, there is an ease of angling of the channels relative to each other, as the channels may be only connected by the relatively thin membrane at junction 39. This membrane allows the channels to readily bend relative to one another with relatively little stress on the port.

If desired, additional instruments may be inserted through the other channels 30a and 30c in a similar manner, such that all of the original proximal ends 32a-32c may extend through the main conduit 50 and distal to the expansion member 60 within the body cavity. In this manner, multiple instruments may be guided into the bodily cavity by their own individual channel 30a-30c, and may be maintained in separate channels at least through the surgical incision 110 and the expansion member 60, thereby facilitating advancement and positioning of multiple components. Notably, when a channel is not in use by an instrument, it may be sealed to prevent escape of insufflation gas, e.g., using a plug or by including a valve at the opening of the channel.

In alternative embodiments, fewer than all of the channels 30a-30c may be evertable. For example, only one or two of the channels 30a-30c may be evertable in the manner shown with respect to the channel 30b in FIG. 6. Further, one or more of the channels 30a-30c may be more rigid and incapable of eversion, thus remaining entirely outside of the patient at all times. Further, as noted above, while three channels 30a-30c are depicted, it will be appreciated that greater or fewer channels may be provided, and their shapes and placements may be varied, without departing from the spirit of the present embodiments.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

I claim:

1. A surgical access port, comprising:
   a plurality of channels each having separate proximal and distal ends, and a lumen extending therebetween,
   where a first channel of the plurality of channels comprises a first state in which the proximal end is positioned proximal to the distal end, and
   where the first channel comprises a second state in which the first channel is everted by advancing the proximal end through the distal end, such that the proximal end is positioned distally beyond the distal end.

2. The surgical access port of claim 1 wherein the proximal end of the first channel has a first outer diameter and the distal end of the first channel has a second inner diameter, where the first outer diameter is smaller than the second inner diameter.

3. The surgical access port of claim 1, wherein, a second channel of the plurality of channels and a third channel of the plurality of channels are provided,
   where each of the, second and third channels comprises a first state in which the respective proximal ends are each positioned proximal to the respective distal ends, and
   where each of the, second and third channels further comprises a second state in which the, second and third channels are everted by advancing the respective proximal ends through the respective distal ends.

4. The surgical access port of claim 1 further comprising at least one expansion member having contracted and expanded states, where the expansion member is configured for insertion through a surgical incision in the contracted state and expands to a diameter larger than the surgical incision in the expanded state.

5. The surgical access port of claim 4, wherein the expansion member comprises a toroidal balloon.

6. The surgical access port of claim 5 further comprising an inflation port disposed proximal to the toroidal balloon and configured to inflate the toroidal balloon to the expanded state, wherein the inflation port is positioned adjacent to the first channel when the first channel is in the first state.

7. The surgical access port of claim 1, further comprising:
   a proximal region, wherein the first channel is positioned within the proximal region in the first state;
   a junction where the distal end of the first channel is disposed;
   a distal region, wherein at least one expansion member having contracted and expanded states is positioned along the distal region; and
   a main conduit having a lumen, the main conduit extending from the junction distally through the at least one expansion member,
   where the lumen of the first channel is in fluid communication with the lumen of the main conduit, and
   where, in the second state, the proximal end of the first channel is inserted distally through the lumen of the main conduit and distally through the at least one expansion member.

8. The surgical access port of claim 7, further comprising a first taper disposed between the junction and a plug region of the main conduit that aligns with a surgical incision.

9. The surgical access port of claim 7, further comprising at least one membrane disposed at least partially over the at least one expansion member, wherein when the at least one expansion member is in the expanded state, the at least one membrane forms a taper between the at least one expansion member and a plug region of the main conduit that aligns with a surgical incision.

10. A method for accessing a bodily cavity, the method comprising:
   providing a surgical access port comprising a plurality of channels each having separate proximal and distal ends, and a lumen extending therebetween, where the surgical access port is provided with a first channel of the plurality of channels in a first state in which the proximal end is positioned proximal to the distal end of the first channel;
   positioning the surgical access port so that at least a portion of the surgical access port is disposed with a surgical incision, where the proximal end of the first channel is positioned proximal to the surgical incision in the first state; and
   everting the first channel to achieve a second state in which the proximal end is advanced through the distal end, such that the proximal end is positioned distally beyond the distal end.

11. The method of claim 10, where the proximal end of the first channel has a first outer diameter and the distal end of the first channel has a second inner diameter, where the first outer diameter is smaller than the second inner diameter.

12. The method of claim 10, where the surgical access port comprises at least one expansion member, the method further comprising:
   advancing the at least one expansion member through the surgical incision in the contracted state; and
   expanding the at least one expansion member to an expanded state having a diameter larger than the surgical incision.

13. The method of claim 12, where the at least one expansion member comprises a toroidal balloon.

14. The method of claim 10, where the surgical access port comprises a proximal region in which the first channel is positioned in the first state, a junction where the distal end of the first channel is disposed, and a distal region where at least one expansion member is positioned, the method further comprising:
   providing a main conduit having a lumen, the main conduit extending from the junction distally through the expansion member, where the lumen of the first channel is in fluid communication with the lumen of the main conduit; and
   inserting the proximal end of the first channel distally through the lumen of the main conduit and distally through the expansion member to achieve the second state.

15. A surgical access port, comprising:
   a plurality of channels each having separate proximal and distal ends, and a lumen extending therebetween;
   a toroidal balloon having contracted and expanded states, where the toroidal balloon is configured for insertion through a surgical incision in the contracted state and expands to a diameter larger that the surgical incision in the expanded state; and
   an inflation port disposed proximal to the toroidal balloon and configured to inflate the toroidal balloon to the expanded state,
   where the toroidal balloon comprises a material adapted to flex and conform to a tissue distal to the surgical incision in the expanded state,
   where a first channel of the plurality of channels comprises a first state in which the proximal end is positioned proximal to the distal end, and where the first channel comprises a second state in which the first channel is everted by advancing the proximal end through the distal end, such that the proximal end is positioned distally beyond the distal end.

16. The surgical access port of claim 15 wherein the proximal end of the first channel has a first outer diameter and the distal end of the first channel has a second inner diameter, where the first outer diameter is smaller than the second inner diameter.

17. The surgical access port of claim 15, further comprising:
   a proximal region, wherein the first channel is positioned within the proximal
   a junction where the distal end of the first channel is disposed;
   a distal region along which the toroidal balloon is positioned; and
   a main conduit having a lumen, the main conduit extending from the junction distally through the toroidal balloon,
   where the lumen of the first channel is in fluid communication with the lumen of the main conduit, and
   where, in the second state, the proximal end of the first channel is inserted distally through the lumen of the main conduit and distally through the toroidal balloon.

18. The surgical access port of claim 17, further comprising a first taper disposed between the junction and a plug region of the main conduit that aligns with a surgical incision.

19. The surgical access port of claim 17, further comprising at least one membrane disposed at least partially over the toroidal balloon, wherein when the toroidal balloon is in the expanded state, the at least one membrane forms a second taper between the toroidal balloon and a plug region of the main conduit that aligns with a surgical incision.

* * * * *